US007326533B2

(12) United States Patent
Jucker et al.

(10) Patent No.: US 7,326,533 B2
(45) Date of Patent: Feb. 5, 2008

(54) **DETECTION RPOB SEQUENCES OF *MYCOBACTERIUM TUBERCULOSIS***

(75) Inventors: Markus T. Jucker, Renton, WA (US); Steven T. Brentano, Santee, CA (US); Francisco D. Delgado, San Diego, CA (US); Philippe Cleuziat, L'Isle d'Abeau (FR)

(73) Assignees: Gen-Probe Incorporated, San Diego, CA (US); BloMorloux S.A., Marcy-l' Etolle (FR)

( * ) Notice: Subject to any disclaimer, the term of this patent is extended or adjusted under 35 U.S.C. 154(b) by 0 days.

(21) Appl. No.: 11/495,262

(22) Filed: Jul. 27, 2006

(65) Prior Publication Data

US 2006/0263823 A1 Nov. 23, 2006

Related U.S. Application Data

(62) Division of application No. 10/245,988, filed on Sep. 18, 2002, now Pat. No. 7,094,542.

(60) Provisional application No. 60/323,485, filed on Sep. 18, 2001.

(51) Int. Cl.
*C12Q 1/68* (2006.01)
*C07H 21/04* (2006.01)

(52) U.S. Cl. ...................... 435/6; 536/24.3; 536/24.32; 536/24.33

(58) Field of Classification Search ..................... None
See application file for complete search history.

(56) References Cited

U.S. PATENT DOCUMENTS

| | | | |
|---|---|---|---|
| 5,643,723 A * | 7/1997 | Persing et al. ................. 435/6 | |
| 5,851,763 A | 12/1998 | Heym et al. | |
| 6,228,575 B1 | 5/2001 | Gingeras et al. | |
| 6,242,584 B1 | 6/2001 | Kook et al. | |
| 6,329,138 B1 | 12/2001 | De Beenhouwer et al. | |
| 6,410,235 B1 | 6/2002 | Weindel et al. | |
| 6,642,000 B1 | 11/2003 | Strizhkov et al. | |
| 6,696,255 B2 | 2/2004 | Dattagupta | |
| 6,709,815 B1 | 3/2004 | Dong et al. | |
| 6,815,165 B2 | 11/2004 | Lee et al. | |
| 6,951,718 B1 | 10/2005 | Lee et al. | |
| 7,060,436 B2 | 6/2006 | Lyamichev et al. | |
| 7,060,441 B2 | 6/2006 | Bourget et al. | |
| 7,067,643 B2 | 6/2006 | Dahlberg et al. | |
| 7,094,542 B2 | 8/2006 | Jucker et al. | |
| 7,101,672 B2 | 9/2006 | Dong et al. | |
| 7,108,968 B2 | 9/2006 | Gingeras et al. | |
| 2004/0110129 A1 | 6/2004 | Fischer et al. | |
| 2006/0204970 A1 | 9/2006 | Gingeras et al. | |

FOREIGN PATENT DOCUMENTS

| | | |
|---|---|---|
| EP | 0962536 A1 | 12/1999 |
| EP | 1076099 A2 | 2/2001 |
| WO | 9533074 A1 | 12/1995 |
| WO | 9533851 A2 | 12/1995 |
| WO | 0043545 A2 | 7/2000 |
| WO | 0134842 A2 | 5/2001 |
| WO | 0166797 A2 | 9/2001 |

OTHER PUBLICATIONS

Cole et al., "Deciphering the biology of *Mycobacterium tuberculosis* from the complete genome sequence," Nature, 1998, 393(11):537-544, MacMillan Journals Ltd., London, GB.
Jonas et al., "Detection of *Mycobacterium tuberculosis* by molecular methods," Clin. Lab Med., 1997, 17(1):119-128, W B Saunders, Philadelphia PA.
Stinear et al., "Identification of *Mycobacterium ulcerans* in the Environment from Regions in Southeast Australia in Which It Is Endemic with Sequence Capture-PCR," Appl. Environ. Microbiol., Aug. 2000, pp. 3206-3213, vol. 66, No. 8, American Society for Microbiology, USA.

* cited by examiner

*Primary Examiner*—BJ Forman
*Assistant Examiner*—Amanda Shaw
(74) *Attorney, Agent, or Firm*—Christine A. Gritzmacher

(57) ABSTRACT

A method of detecting rpoB sequences of *Mycobacterium tuberculosis* present in a biological sample that includes steps of amplifying the *M. tuberculosis* rpoB sequence in vitro in a nucleic acid amplification mixture that includes specific disclosed primer sequences, and detecting the amplified sequences by using probes that provide information by their specific hybridization to portions of the amplified nucleic acid is disclosed. Compositions for amplifying and detecting in vitro the rpoB sequences of *M. tuberculosis* in a sample are disclosed.

15 Claims, No Drawings

DETECTION RPOB SEQUENCES OF MYCOBACTERIUM TUBERCULOSIS

RELATED APPLICATIONS

This application is a divisional of application Ser. No. 10/245,988, filed Sep. 18, 2002, now U.S. Pat. No. 7,094,542, issued Aug. 22, 2006, which claims the benefit under 35 U.S.C. 119(e) of provisional application No. 60/323,485, filed Sep. 18, 2001, both of which are incorporated by reference.

FIELD OF THE INVENTION

This invention relates to in vitro diagnostic detection of pathogenic bacteria, and specifically relates to compositions and assays for detecting nucleic acid sequences associated with rifampin resistance of *Mycobacterium Tuberculosis* by using in vitro nucleic acid amplification of the rpoB gene and detection of amplified products.

BACKGROUND OF THE INVENTION

Rifampin (RIF), an antibiotic synthesized from rifamycin B, is a key component of drug therapy against *Mycobacterium tuberculosis*. Rifampin has a unique site of action on the beta subunit of prokaryotic RNA polymerase. In *Escherichia coli*, missense mutations and short deletions in the central region of the RNA polymerase subunit gene (rpoB) result in strains resistant to rifampin (Lisityn et al., 1984, *Mol. Gen. Genet.* 196: 173-174). Similarly, in *M. tuberculosis* a wide variety of mutations in the rpoB gene have been identified that confer rifampin resistance (Telenti et al., 1993, *Lancet* 341: 647-650). More than 90% of rifampin-resistant *M. tuberculosis* isolates are also resistant to isoniazid, and, therefore, rifampin resistance is a valuable surrogate marker for multiple drug resistance. Thus, there is a need for tests that can detect rapidly the genetic basis for rifampin resistance for diagnosis that leads to appropriate treatment of infected individuals.

Early detection of drug resistance in clinical *M. tuberculosis* isolates is crucial for appropriate treatment and to prevent the spread of resistant strains. Conventional methods of detecting drug-resistance by growth of *M. tuberculosis* on solid media, and more recent methods that rely on growth in liquid media have provided susceptibility results in 3 days to over 4 weeks (Rusch-Gerdes et al., 1999, *J. Clin. Microbiol.* 37: 45-48).

Genetic techniques that rely on the polymerase chain reaction (PCR) have been devised to detect rifampin resistance. Such techniques include direct sequencing of PCR products, single strand conformation polymorphism analysis, heteroduplexing and dideoxy fingerprinting (Telenti et al., 1993, *Lancet* 342: 841-844; Williams et al., 1994, *Antimicrobial Agents Chemotherapy* 38: 2380-2386; De Beenhouwer, 1995, *Tubercle and lung disease* 76: 425-430). Other assays and reagents for detecting resistance to rifampin in *M. tuberculosis* isolates or identifying Mycobacteria species using rpoB gene have been previously disclosed, for example, in U.S. Pat. No. 5,643,723 (Persing et al.), U.S. Pat. No. 5,851,763 (Heym et al.), U.S. Pat. No. 6,228,575 (Gingeras et al.), and U.S. Pat. No. 6,242,584 (Kook et al.).

The present invention provides compositions and simple diagnostic methods to detect rifampin resistance in *M. tuberculosis* that may be present in a clinical sample.

SUMMARY OF THE INVENTION

According to one aspect of the invention, there is provided a method of detecting rpoB sequences of *Mycobacterium tuberculosis* present in a biological sample. The method includes the steps of providing a biological sample containing nucleic acid from *M. tuberculosis* comprising a rpoB sequence; amplifying the rpoB sequence in an in vitro nucleic acid amplification reaction mixture comprising at least one polymerase activity, and at least two primers selected from the group consisting of SEQ ID NO:2 with SEQ ID NO: 3, SEQ ID NO:2 with SEQ ID NO:8, and SEQ ID NO:10 with SEQ ID NO:11, to produce amplified nucleic acid containing a rpoB sequence; optionally fragmenting the amplified nucleic acid; hybridizing the amplified nucleic acid to at least one detection probe that hybridizes specifically to *M. tuberculosis* sequences; and detecting the amplified nucleic acid hybridized to at least one detection probe by detecting a label associated with the amplified nucleic acid. In one embodiment, before the amplifying step, the method also includes the steps of adding to the biological sample at least one capture oligomer comprising a sequence contained in SEQ ID NO:5, SEQ ID NO:6 or SEQ ID NO:9 that specifically hybridizes to a *M. tuberculosis* sequence, and an immobilized nucleic acid that hybridizes to a 3' tail sequence of the capture oligomer; hybridizing the nucleic acid from *M. tuberculosis*, the capture oligomer, and the immobilized nucleic acid to produce a hybridization complex comprising the nucleic acid from *M. tuberculosis*, the capture oligonucleotide, and the immobilized nucleic acid; and separating the hybridization complex from other components of the biological sample. In another embodiment, the detecting step uses at least one detection probe that hybridizes specifically to a rpoB sequence. Another embodiment uses at least one detection probe consisting of the sequence of SEQ ID NO:4 or SEQ ID NO:12. Another embodiment, in the detecting step, uses a plurality of detection probes in a DNA probe array, wherein at least one detection probe in the array hybridizes specifically to a rpoB sequence. In one embodiment, the amplifying step uses primers of SEQ ID NO:2 with SEQ ID NO:3, and a helper oligomer consisting of SEQ ID NO:1. In another embodiment, the amplifying step uses primers of SEQ ID NO:2 with SEQ ID NO:8, and a helper oligomer consisting of SEQ ID NO:1. Another embodiment uses primers of SEQ ID NO:10 with SEQ ID NO:11. In one embodiment, the amplifying step uses a transcription-mediated amplification reaction mixture, whereas in another embodiment, the amplifying step uses a polymerase chain reaction amplification reaction mixture. In one embodiment, the optional fragmenting step includes chemically fragmenting the amplified nucleic acid and fluorescently labeling fragments of the amplified nucleic acid.

Other aspects of the invention include various compositions for detecting a rpoB sequence of *M. tuberculosis*. One composition includes oligonucleotides consisting of SEQ ID NO:2, SEQ ID NO:3, and SEQ ID NO:4. Another composition includes oligonucleotides consisting of SEQ ID NO:2, SEQ ID NO:3, and a DNA probe array wherein at least one detection probe in the array hybridizes specifically to a rpoB sequence. Another embodiment is a composition that includes oligonucleotides consisting of SEQ ID NO:2, SEQ ID NO:8, and SEQ ID NO:4. Yet another embodiment is a composition that includes oligonucleotides consisting of SEQ ID NO:2, SEQ ID NO:8, and a DNA probe array wherein at least one detection probe in the array hybridizes specifically to a rpoB sequence. Another composition of the invention includes oligonucleotides consisting of SEQ ID NO:10, SEQ ID NO:11, and SEQ ID NO:12.

Another aspect of the invention is a kit that includes at least two oligonucleotides having sequences selected from the group consisting of SEQ ID NO:1, SEQ ID NO:2, SEQ ID NO:3, SEQ ID NO:4, SEQ ID NO:8, SEQ ID NO:10, SEQ ID NO:11, and SEQ ID NO:12.

DETAILED DESCRIPTION

The present invention includes methods of detecting rpoB sequences for *Mycobacterium tuberculosis* present in biological samples derived from humans, preferably in processed sputum samples. The present invention also includes compositions that include nucleic acid capture oligomers that specifically hybridize to *M. tuberculosis* sequences present in a biological sample, thereby providing a means for capturing the target sequence from the sample components, nucleic acid amplification oligomers (or primers) that specifically amplify selected portions of the rpoB DNA sequences, and nucleic acid probe oligomers (or detection probes) for detecting such amplified sequences.

The nucleic acid sequences of this invention are useful for capturing, amplifying and detecting mutations of rpoB gene for *M. tuberculosis* present in a biological sample. The methods of the present invention are important for diagnosis of a drug resistance phenotype of *M. tuberculosis* by giving the clinician information useful in determining appropriate treatment of the *M. tuberculosis* infected patient.

The following definitions are provided to aid in understanding the described invention.

By "biological sample" is meant any tissue or material derived from a living or dead human which may contain *M. tuberculosis* nucleic acid. Samples include, for example, sputum, respiratory tissue or exudates, peripheral blood, plasma or serum, cervical swab samples, biopsy tissue, gastrointestinal tissue, urine, feces, semen or other body fluids, tissues or materials. Samples also include bacterial cultures (from liquid or solid media) and environmental samples. A biological sample may be treated to physically disrupt tissue or cell structure, thus releasing intracellular components into a solution which may contain enzymes, buffers, salts, detergents and the like which are used to prepare the sample for analysis.

By "nucleic acid" is meant a multimeric compound comprising nucleosides or nucleoside analogs which have nitrogenous heterocyclic bases, or base analogs, where the nucleosides are covalently linked via a backbone structure to form a polynucleotide. Conventional RNA, DNA, and analogs of RNA and DNA are included in this term. A nucleic acid backbone may comprise a variety of known linkages known, including one or more of sugar-phosphodiester linkages, peptide-nucleic acid bonds ("peptide nucleic acids"; PCT No. WO 95/32305 (Hydig-Hielsen et al.)), phosphorothioate linkages, methylphosphonate linkages or combinations of known linkages. Sugar moieties of the nucleic acid may be ribose or deoxyribose, or similar compounds having known substitutions, e.g., 2' methoxy and/or 2' halide substitutions. Nitrogenous bases may be conventional bases (A, G, C, T, U), known base analogs (e.g., inosine; see *The Biochemistry of the Nucleic Acids* 5-36, Adams et al., ed., 11$^{th}$ ed., 1992), or known derivatives of purine or pyrimidine bases (PCT No. WO 93/13121 (Cook)) and "abasic" residues in which the backbone includes no nitrogenous base for one or more residues (U.S. Pat. No. 5,585,481 (Arnold et al.)). A nucleic acid may comprise only conventional sugars, bases and linkages, as found in RNA and DNA, or may include both conventional components and substitutions (e.g., conventional bases linked via a methoxy backbone, or a nucleic acid including conventional bases and one or more analogs).

By "oligonucleotide" or "oligomer" is meant a nucleic acid having generally less than 1,000 residues, including those in a size range having a lower limit of about 2 to 5 nucleotide residues and an upper limit of about 500 to 900 nucleotide residues. Oligomers may be in a size range having a lower limit of about 5 to about 15 residues and an upper limit of about 50 to 600 residues; and preferably, in a size range having a lower limit of about 10 residues and an upper limit of about 100 residues. Oligomers can be purified from natural sources, but generally are synthesized in vitro using well-known methods.

By "amplification oligonucleotide" or "amplification oligomer" is meant an oligonucleotide or oligomer that hybridizes to a target nucleic acid, or its complement, and participates in an in vitro nucleic acid amplification reaction. These may be called "primers" because they initiate polymerization from a template by enzymatic activity that adds nucleotide monomers at their 3' ends. An amplification oligonucleotide generally contains at least 10 to 12 contiguous bases that are complementary to a region of the target nucleic acid sequence (or its complementary strand). The contiguous bases are preferably at least 80%, more preferably at least 90% complementary to the sequence to which the amplification oligonucleotide binds. An amplification oligonucleotide is preferably about 10 to about 60 bases long and may include modified nucleotides, base analogs or additional functional sequences, such as a 5' promoter sequence recognized by an RNA polymerase (such amplification oligonucleotides may be called "promoter primers").

Those skilled in the art will appreciate that any oligomer that can function as a primer can be modified to include a 5' promoter sequence, and thus function as a promoter primer. Similarly, any promoter primer can serve as a primer, independent of its promoter sequence.

By "amplification" is meant an in vitro procedure for obtaining multiple copies of a target nucleic acid sequence or its complement or fragments thereof. In vitro amplification refers to production of an amplified nucleic acid that may contain less than the complete target region sequence or its complement. Known amplification methods include, for example, transcription-mediated amplification (TMA), replicase-mediated amplification, polymerase chain reaction (PCR) amplification, ligase chain reaction (LCR) amplification and strand-displacement amplification (SDA). Replicase-mediated amplification uses self-replicating RNA molecules, and a replicase such as Q Beta-replicase (U.S. Pat. No. 4,786,600 (Kramer et al.) and U.S. Pat. No. 5,112,734 (Lizardi et al.)). PCR amplification uses thermal cycling with a DNA polymerase and, usually, two or more primers to synthesize multiple copies of two complementary DNA strands (Mullis et al., 1987, *Methods in Enzymology* 155: 335-350; U.S. Pat. Nos. 4,683,195, 4,683,202, and 4,800,159 (Mullis et al.)). LCR amplification uses at least four separate oligonucleotides to amplify a target and its complementary strand by using multiple cycles of hybridization, ligation, and denaturation (EP Pat. No. 0320308 (Wang et al.)). SDA uses a primer that contains a recognition site for a restriction endonuclease which will nick one strand of a hemimodified DNA duplex that includes the target sequence, followed by a series of primer extension and strand displacement steps to amplify DNA (U.S. Pat. No. 5,422,252 (Walker et al.)). Transcription-mediated amplification (TMA) is used in preferred embodiments of the present invention. Those skilled in the art will understand that the oligonucleotide sequences of the present invention may be readily used in any in vitro amplification method based on primer extension.

By "transcription-mediated amplification" or "transcription-associated amplification" is meant nucleic acid amplification that uses an RNA polymerase to produce multiple RNA transcripts from a nucleic acid template. TMA generally uses an RNA polymerase activity, a DNA polymerase activity, deoxyribonucleoside triphosphates, ribonucleoside triphosphates, and a promoter primer and a second primer, and optionally may include one or more additional oligonucleotides (sometimes referred to as "helper" or "displacer" oligonucleotides). These amplification methods are well known in the art, as described in detail elsewhere (U.S. Pat. Nos. 5,399,491 and 5,554,516 (Kacian et al.), U.S. Pat. No. 5,786,183 (Ryder et al.), PCT No. WO 93/22461 (Kacian et al.); U.S. Pat. No. 5,437,990 (Burg et al.); PCT Nos. WO 88/01302 and WO 88/10315 (Gingeras et al.); U.S. Pat. No. 5,130,238 (Malek et al.); U.S. Pat. Nos. 4,868,105 and 5,124,246 (Urdea et al.); PCT No. WO 94/03472 (McDonough et al.); and PCT No. WO 95/03430 (Ryder et al.)). Preferred TMA methods have been disclosed in U.S. Pat. Nos. 5,399,491, 5,554,516 and 5,786,183, and PCT No. WO 93/22461.

By "probe" is meant a nucleic acid oligomer that hybridizes specifically to a target sequence in a nucleic acid or its complement, preferably in an amplified nucleic acid, under conditions that promote hybridization, thereby allowing detection of the target or amplified nucleic acid. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). A probe's "target" generally refers to a sequence in (i.e., a subset of) a larger nucleic acid sequence that hybridizes specifically to at least a portion of the probe sequence by standard hydrogen bonding (base pairing). Sequences that are "sufficiently complementary" allow stable hybridization of a probe oligomer to a target sequence, even if the two sequences are not completely complementary. A probe may be labeled or unlabeled, depending on the detection method used, which methods are well known in the art.

By "sufficiently complementary" is meant a contiguous nucleic acid base sequence that hybridizes to another base sequence by hydrogen bonding between a series of complementary bases under hybridization conditions. Sequences may be complementary at each position in a sequence using standard base pairing (i.e., G:C, A:T or A:U pairing) or may contain one or more residues that are not complementary by standard hydrogen bonding (including abasic residues), but in which the entire base sequence is capable of specifically hybridizing with another base sequence in appropriate hybridization conditions. Contiguous bases are preferably at least about 80%, more preferably at least about 90% complementary to a sequence to which an oligomer specifically hybridizes. Appropriate hybridization conditions are well known to those skilled in the art, can be predicted readily based on sequence composition and conditions, or can be determined empirically by using routine testing (Sambrook et al., *Molecular Cloning, A Laboratory Manual*, $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly at §§ 9.50-9.51, 11.12-11.13, 11.45-11.47 and 11.55-11.57).

By "capture oligonucleotide" or "capture oligomer" or "capture probe" is meant at least one nucleic acid oligomer that provides means for specifically joining a target sequence and an immobilized oligomer based on base pair hybridization (U.S. Pat. No. 6,110,678 (Weisburg et al.)). Generally, a capture oligomer includes two binding regions: a target-specific binding region and an immobilized probe-specific binding region.

By "immobilized probe" or "immobilized oligomer" is meant a nucleic acid that joins, directly or indirectly, a capture oligomer to a solid support. An immobilized probe is an oligonucleotide joined to a solid support provides a means for separating a bound target sequence from other sample components. Suitable solid supports include matrices and particles in solution, made of any known material (e.g., nitrocellulose, nylon, glass, polyacrylate, mixed polymers, polystyrene, silane polypropylene and metal particles, preferably paramagnetic particles). Preferred supports are monodisperse paramagnetic spheres (uniform in size ±about 5%), to which an immobilized probe is stably joined directly (e.g., via direct covalent linkage, chelation, or ionic interaction), or indirectly (e.g., via hybridization with one or more linkers), thus permitting hybridization to another nucleic acid in solution.

By "separating" or "purifying" is meant that one or more components of the biological sample are removed from other sample components. Sample components generally are an aqueous solution that includes nucleic acids and other materials (e.g., proteins, carbohydrates, lipids and/or nucleic acids). A separating or purifying step removes at least about 70%, preferably at least about 90%, and more preferably at least about 95% of the other sample components.

By "label" is meant a molecular moiety or compound that can be detected or can lead to a detectable response. A label is joined, directly or indirectly, to a nucleic acid probe or to a nucleic acid to be detected (e.g., an amplified nucleic acid). Direct labeling can occur through bonds or interactions that link the label to the probe (e.g., via covalent bonds or non-covalent interactions). Indirect labeling can occur through use of a bridging moiety or linker, such as additional oligonucleotide(s), which is either directly or indirectly labeled. Bridging moieties can be used to amplify detectable signal. Labels can be any known detectable moiety (e.g., radionuclide, ligand, such as biotin or avidin, enzyme, enzyme substrate, reactive group, chromophore, e.g., dye or colored particle, luminescent compound, including bioluminescent, phosphorescent, chemiluminescent and fluorescent compounds). Preferably, the label on a labeled probe is detectable in a homogeneous assay system (i.e., in a mixture, bound labeled probe exhibits a detectable change compared to unbound labeled probe). Preferred chemiluminscent labels and their use in homogenous detection assays have been described in detail (U.S. Pat. No. 5,283,174 (Arnold Jr., et al.), U.S. Pat. No. 5,656,207 (Woodhead et al.), U.S. Pat. No. 5,658,737 (Nelson et al.) and U.S. Pat. No. 5,639,604 (Arnold Jr., et al.)). Such labels include acridinium ester ("AE") compounds, e.g., standard AE or its derivatives. A homogeneous detectable label has the advantage of being detectable without physically separating hybridized from unhybridized label or labeled probe. Methods of attaching labels to nucleic acids and detecting labels are well known in the art (Sambrook et al., *Molecular Cloning, A Laboratory Manual*, 2nd ed. (Cold Spring Harbor Laboratory Press, Cold Spring Habor, N.Y., 1989), Chapter 10; U.S. Pat. No. 5,731,148 (Becker et al.), U.S. Pat No. 5,658,737 (Nelson et al.), U.S. Pat No. 5,656,207 (Woodhead et al.), U.S. Pat. No.

5,547,842 (Hogan et al.), U.S. Pat No. 5,283,174 (Arnold Jr., et al.) and U.S. Pat No. 4,581,333 (Kourilsky at al.)).

By "DNA probe array", is meant a solid support on which are immobilized at least 2, and preferably 10 or more, different capture oligonucleotide. Examples of such DNA probe arrays are well known in the art (Ramsay, 1998, *Nature Biotech.*16: 40-44; Cheng et al., 1996, *Molec. diagnosis* 1(3): 183-200; Livache et al., 1994, *Nucl. Acids Res.* 22(15): 2915-2921; Cheng et al., 1998, *Nature Biotech.* 16: 541-546; U.S. Pat. Nos. 4,981,783 (Augenlicht), U.S. Pat No. 5,700,637 (Southern), U.S. Pat No. 5,445,934 and U.S. Pat No. 5,744,305 (Fodor), and U.S. Pat No. 5,807,522 (Brown)).

By "consisting essentially of" is meant that additional component(s), composition(s) or method step(s) that do not materially change the basic and novel characteristics of the invention may be included in the compositions, kits or methods of the present invention. Such characteristics include the ability to detect rpoB sequences of *M. tuberculosis* in a biological sample at about 20 to 200 or more copies per sample. Any component, composition, or method step that has a material effect on the invention's basic characteristics would fall outside of this term.

Unless defined otherwise, all scientific and technical terms used herein have the same meaning as commonly understood by those skilled in the relevant art. General definitions are provided, for example, in *Dictionary of Microbiology and Molecular Biology,* 2nd ed. (Singleton et al., 1994, John Wiley & Sons, New York, N.Y.) or *The Harper Collins Dictionary of Biology* (Hale & Marham, 1991, Harper Perennial, New York, N.Y.). Unless mentioned otherwise, the techniques employed or contemplated herein are well known standard methods in the art.

The present invention includes compositions (nucleic acid capture oligomers, amplification oligomers and probes) and methods for detecting *M. tuberculosis* rpoB nucleic acid in a human biological sample. To select appropriate DNA sequences for such use, known rpoB sequences from different *Mycobacterium* isolates, including known mutations, available from publicly accessible databases (e.g., GenBank) were aligned by matching regions of the same or similar sequences and compared using well known molecular biology techniques. Although use of algorithms may facilitate sequence comparisons, those skilled in the art can readily perform such comparisons manually and visually. Generally, sequence portions containing relatively few variants between the compared sequences were chosen as a basis for designing synthetic oligomers suitable for use in capture and amplification of *M. tuberculosis* nucleic acid sequences in the rpoB region and detection of amplified sequences. Other considerations in designing oligomers included the relative GC content which affects $T_m$ of the sequence and the relative absence of predicted secondary structure within a sequence, all well known in the art. Based on these analyses, the oligomers having sequences of SEQ ID NO:1 to SEQ ID NO:6 and SEQ ID NO:8 to SEQ ID NO:12 were designed and synthesized.

Target capture may be included to increase the concentration or purity of the target nucleic acid before in vitro amplification. Preferably, target capture involves a relatively simple method of hybridizing and isolating the target nucleic acid, as described in detail elsewhere (U.S. Pat. No. 6,110,678 and PCT No. WO 98/50583 (Weisburg et al.)). Briefly, a sample that potentially contains *M. tuberculosis* DNA is contacted with a capture oligorner containing a sequence specific for hybridization to *M. tuberculosis* DNA, and an immobilized oligonucleotide attached to a solid support that can hybridize to another portion of the capture oligomer under appropriate hybridization conditions. Following hybridization of the capture oligomer to the *M. tuberculosis* DNA and then to the immobilized oligonucleotide, the hybridization complex attached to the solid support is separated from other sample components. Then, the *M. tuberculosis* target nucleic acid linked to the solid support is washed and rpoB sequences are amplified in an in vitro amplification reaction.

The capture oligomer sequence includes a 5' target-binding sequence that binds specifically to the *M. tuberculosis* DNA target sequence, and a 3' tail sequence (e.g., poly-dA) that binds to the complementary immobilized sequence (e.g., poly-dT) on the solid support. A capture oligomer may use any backbone to link the base sequence, including standard deoxyribose-phosphate linkages and O-methoxy linkages. Preferred capture oligomers have sequences of: GGCCACCATCGAATATCTGGTCCGCTTGCACTTT$(A)_{30}$ (SEQ ID NO:5), CATGTCGCGGATGGAGCGGGTGGTC$(A)_{30}$ (SEQ ID NO:6), and CATCGMTATCTGGTCCGCTTGCAC$(A)_{30}$ (SEQ ID NO:9).

Amplifying the captured rpoB region can be accomplished using a variety of known nucleic acid amplification reactions, but preferably uses a transcription-mediated amplification (TMA). Using such an in vitro amplification method, many strands of nucleic acid are produced from a single copy of target nucleic acid, thus permitting detection of the target by specifically binding the amplified rpoB sequences to one or more detecting probes. TMA has been described in detail previously (U.S. Pat. Nos. 5,399,491 and 5,554,516 (Kacian et al.)). Briefly, this amplification method uses two types of primers (one being a "promoter primer" that contains a promoter sequence for an RNA polymerase), two enzymes (a reverse transcriptase and an RNA polymerase), substrates (deoxyribonucleoside triphosphates, ribonucleoside triphosphates) and appropriate salts and buffers in solution to produce multiple RNA transcripts from a nucleic acid template. First, a promoter primer hybridizes specifically to its target nucleic acid sequence and reverse transcriptase creates a first strand cDNA by extension from the 3' end of the promoter primer. The cDNA becomes available for hybridization with the second primer by enzymatic activity that degrades the complementary strand (e.g., RNase H activity of the reverse transcriptase) or by localized or complete denaturaton of the duplex. A second primer binds to the cDNA and a new strand of DNA is synthesized from the 3' end of the second primer using reverse transcriptase to create a double-stranded DNA having a functional promoter sequence at one end. RNA polymerase binds to the double-stranded promoter sequence and transcription produces multiple transcripts or "amplicons." Amplicons are used in further steps in the process, each serving as a template for a new round of replication as described above, thus generating large amounts of single-stranded amplified nucleic acid in a substantially isothermal process. For example, about 100 to about 3,000 copies of RNA transcripts are synthesized from a single template.

Primer sequences (e.g., SEQ ID NO: 1 to SEQ ID NO: 3 and SEQ ID NO:8, SEQ ID NO:10 and SEQ ID NO:11) bind specifically to an rpoB target sequence or its complement, but such primer sequences may contain sequences that do not bind to the target sequence or its complement. For example, promoter primers (e.g., SEQ ID NO:2, SEQ ID NO:10) may include a T7 RNA polymerase promoter sequence (SEQ ID NO:7) as a 5' portion of the sequence.

Embodiments of the present invention are described in the examples that follow. Briefly, the methods include the steps of providing a biological sample that potentially contains the target M. tuberculosis rpoB gene, target capture of DNA containing an rpoB sequence, in vitro nucleic acid amplification and detection of the amplified nucleic acid products to determine if an rpoB mutation is present in the amplified nucleic acid. If an rpoB mutation is detected, it indicates that the sample contained a RIF-resistant *M. tuberculosis*. In preferred embodiments that use transcription-mediated amplification (TMA), the amplification mixture includes the captured target DNA, at least one T7 promoter primer that includes a target-specific sequence and a T7 promoter sequence, at least one second primer that hybridizes specifically to a first strand cDNA made from the target using the T7 promoter primer, and substrates and cofactors for enzymatic polymerization by reverse transcriptase and T7 RNA polymerase. The captured target does not have to be separated from the solid support for use in the TMA reaction. The functional T7 promoter sequence combined with T7 RNA polymerase produces multiple transcripts which can be detected using any of a variety of known methods, including hybridizing specifically the amplified products, or portions thereof, to one or more complementary probe sequences. In some embodiments, a labeled probe is used to detect the amplified products, whereas in other embodiments, the amplified products are labeled and hybridized to immobilized probes, preferably to an array of many probes. The hybridization complex of the probe and amplified product is detected. When an array of different probes is used, the pattern of hybridization on the array indicates the sequence of the amplified rpoB gene, which provides information on whether a rpoB mutation of *M. tuberculosis* is present in the sample assayed.

Typical assay conditions described as follows.

Sample preparation. A sample (e.g., 0.5 ml of sputum sediment or bacterial culture) was mixed with an equal volume of a 2× lysis buffer (e.g., 20 mM HEPES, 0.5% (w/v) lithium lauryl sulfate (LLS), pH 8). To release nucleic acids from the bacteria, the mixture was vortexed in the presence of glass beads, or sonicated for 15 min, and then the mixture was heated at 95° C. for 15 min. For positive control reactions, an equal volume of water or buffer containing a known amount of *M. tuberculosis* genomic DNA (gDNA) was used in place of the sputum sediment or bacterial culture. The gDNA was prepared using a combination of standard methods that have been described in detail previously. Briefly, cells were grown in broth to late log phase and treated 18 hr with 1 mg/ml ampicillin and 0.1 mg/ml D-Cycloserine (Crawford et al., 1979, *Infect. Immun.* 24: 979-81). Then, cells were collected and lysed with SDS and treated with Proteinase K to release DNA into an aqueous solution which was extracted twice with sodium perchlorate and a phenol/chloroform mixture, and DNA was spooled out of the solution after adding about two volumes of ethanol (Maniatis et al., *Molecular Cloning, A Laboratory Manual* (Cold Spring Harbor Laboratory Press, Cold Spring Harbor, N.Y., 1982), pp. 280-81 and 458-59; and Marmur, 1961, *J. Mol. Biol.* 3: 209-18).

Target capture. Generally, lysate prepared from a sample was used in the target capture step (U.S. Pat. No. 6,110,678 (Weisburg et al.)). To capture the target *M. tuberculosis* DNA, the mixture included 250 μl of prepared sample lysate, 250 μl of a target capture solution containing 3 pmole of SEQ ID NO:5 and 3 pmole of SEQ ID NO:6 or 3 pmol of SEQ ID NO:9, and 40 μg of paramagnetic particles (0.7-1.05μ, Seradyn, Indianapolis, Ind.) with attached immobilized poly-$dT_{14}$ oligomers (Lund, et al., 1988, *Nuc. Acids Res.*16: 10861-80). The target capture mixture was heated at 60° C. for about 20 min and then cooled to room temperature. A magnetic field was applied for 5 min to attract the magnetic particles with the attached complex containing the target DNA to a location on the reaction container (substantially as described in U.S. Pat. No. 4,895,650 (Wang)). Particles with attached hybridization complexes were washed twice with 1 ml of a washing buffer (10 mM HEPES, 6.5 mM NaOH, 1 mM EDTA, 150 mM NaCl, 0.1% (w/v) sodium lauryl sulfate) by resuspending the particles in the washing buffer and then repeating the magnetic separation step.

Amplification. Transcription mediated amplification was performed substantially as described previously (U.S. Pat. Nos. 5,399,491 and 5,554,516 (Kacian et al.)). Washed particles from the target capture step were suspended in 75 μl of amplification reagent solution (0.08 mM rUTP, 1.3 mM rATP, 4 mM rCTP, 6 mM rGTP, 1.3 mM each dNTP, 66 mM Tris, 17.3 mM $MgCl_2$). The relatively low concentration of rUTP is important for amplification efficiency of the rpoB target DNA. At least two amplification oligomers were included in the amplification reaction, i.e., at least one promoter primer and a second primer, usually at 0.08 μM final concentration. (Amplification oligomers may also include helper or displacer oligomers and may be hybridized to the target before other amplification reagents are added to the mixture.) The reaction mixture was covered with a layer (200 μl) of inert oil to prevent evaporation and incubated at 42° C. for 5 min. Then 25 μl of enzyme reagent was added (about 1750 U of MMLV reverse transcriptase and 400 U of T7 RNA polymerase per reaction, in a buffer containing 50 mM HEPES, 1 mM EDTA, 10% (v/v) t-octylphenoxypolyethoxyethanol (TRITON™ X-100), 120 mM KCl, 20% (v/v) glycerol). (One unit of MMLV reverse transcriptase incorporates 1 nmol of dTTP in 10 min at 37° C. using a polyA template primed with 200-400 μM oligo(dT); and one unit of T7 RNA polymerase incorporates 1 nmol of ATP into RNA in 1 hr at 37° C. using a DNA template containing a T7 promoter sequence.) After mixing gently, the reaction was incubated at 42° C. for 1 hr. Negative controls consisted of all of the same reagents but substituting an equal volume of water or buffer that contained no target.

Detection. In some cases, amplified *M. tuberculosis* sequences were detected using an acridinium ester (AE)-labeled probe (e.g., 5'-GTTGTTCTGGTCCATGAA (SEQ ID NO:4)) which was detected by chemiluminescence in a luminometer (e.g., LEADER™ luminometer, Gen-Probe Incorporated, San Diego, Calif.) and signal is expressed in relative light units (RLU) substantially as described previously (U.S. Pat. No. 5,658,737 (Nelson et al.) at column 25, lines 27-46; Nelson et al., 1996, *Biochem.* 35: 8429-8438, at 8432). Generally, the average (mean) of detected RLU for replicate assays are reported. In a preferred embodiment, the labeled detection probe has the base sequence of SEQ ID NO:4 linked by a 2'-O-methoxy backbone.

In other cases, the amplified sequences were detected on an immobilized array of DNA probes specific for detection of *M. tuberculosis* rpoB sequences, as described in detail previously (Troesch et. al., 1999, *J. Clin. Microbiol.* 37: 49-55). Amplicons generated by the amplification reaction were labeled with a fluorescent label before hybridization to the array using methods substantially as described in detail elsewhere (PCT Nos. WO 99/65926 and WO 01/44507 (Laayoun et al.)). Briefly 50 μl of amplicons were mixed with 30 mM $MnCl_2$, 30 mM imidazole, 2 mM of 5-(bromomethyl)fluorescein and water (150 μl final volume). After a 30 min incubation at 65° C., free label was eliminated by column chromatography (e.g., using a 6S QIAVAC® column, Qiagen GmbH, according to the manufacturer's instructions).

Hybridization of the probe arrays was performed with the GENECHIP® Fluidics Station (Affymetrix, Santa Clara, Calif.) substantially as previously described (Troesch et al., 1999, *J. Clin. Microbiol.* 37: 49-55). An additional step, antibody staining, allows signal amplification as described elsewhere (PCT No. WO 01/44506 (Laayoun et al.)). Briefly, after hybridization was performed on the DNACHIP®using the protocol of Troesch et al., the DNACHIP® was flushed and a second step of staining was performed using staining solution containing 300 µl of 2 M MES, 2.4 µl of bovine serum albumin (BSA), 6 µl of normal goat IgG, 1.2 µl of anti-fluorescein antibody, and water (600 µl final volume). Anti-fluorescein, rabbit IgG fraction, biotin-XX conjugate, were supplied by Molecular Probes (Eugene, Oreg.); acetylated BSA solution was supplied by GibcoBRL Life Technologies, (Rockville, Md.); and goat IgG (Reagent Grade) was supplied by Sigma Chemical, (St. Louis, Mo.). After a 10 min hybridization, the chip was flushed, washed with a washing buffer containing 6×SSPE, 0.01% polyoxyethylenesorbitan (TWEEN® 20), and a third hybridization step was performed, using second staining solution of 300 µl of 2M MES, 6 µl of BSA and 6 µl of streptavidin, R-phycoerythrin conjugate, and water (600 µl final volume). Streptavidin and R-phycoerythrin conjugate were supplied by Molecular Probes (Eugene, Oreg.). After a 10 min hybridization, the chip was flushed and washed as described above. The analysis to detect the intensity and pattern of fluorescent signals (expressed as relative fluorescence units or RFU) on the hybridized array was performed on the GENECHIP™ instrumentation system (Affymetrix, Santa Clara, Calif.) which comprises a GENECHIP™ fluidics station, a GENEARRAY™ scanner (Hewlett-Packard, Palo Alto, Calif.) and GENECHIP™ analysis software (algorithm to determine nucleotide base calling and the nucleic acid sequence of the amplified nucleic acid). This system generates a report of the rpoB mutations present in the amplified nucleic acid sequences applied to the chip.

The following examples demonstrate embodiments of the present invention.

EXAMPLE 1

Sensitivity of Transcription Mediated Amplification Using *M. tuberculosis*-Specific Oligonucleotides This example shows the sensitivity of the amplification oligonucleotides of the present invention when used in a TMA reaction. Primers were designed to amplify *M. tuberculosis* specifically and not other *Mycobacterium* species. Using the target capture and amplification methods described above, the efficiencies of transcription mediated amplification were tested using the following combination of amplification oligonucleotides: SEQ ID NO:1 (GAC-CACCCAGGACGTG) as a helper oligomer, SEQ ID NO: 2 (AATTTAATACGACTCACTATAGGGAGAC-GATCACACCGCAGACGTTG) as a promoter primer, and SEQ ID NO: 3 (GCTCGCGCTCACGTG) as a primer. Target sequences for this assay were purified gDNA extracted from a lysed bacterial culture of *M. tuberculosis* and provided at 20, 200 or 1000 copies per in vitro amplification reaction. As a negative control, an equal volume of water containing no *M. tuberculosis* DNA was substituted for the gDNA sample in a separate amplification reaction that was processed as for the positive samples. Amplification was assessed based on the detected chemiluminescence (RLU) using a homogeneous detection assay performed substantially as described elsewhere in detail (U.S. Pat. No. 5,283,174 (Arnold Jr., et al.), U.S. Pat No. 5,658,737 (Nelson et al.) and U.S. Pat No. 5,639,604 (Arnold Jr., et al.)). An AE-labeled detection probe of SEQ ID NO:4 (GTTGT-TCTGGTCCATGAA) was mixed with unlabeled probe of the same sequence (ratio of labeled probe/unlabeled probe was 1/5000) to provide a signal within the linear range detectable by the LEADER™ luminometer (Gen-Probe Incorporated, San Diego, Calif.). Signals of $2 \times 10^4$ or greater RLU were considered positive. The RLU results (mean of 10 assays for each assay condition) are shown in Table 1.

These results demonstrate that the amplification reaction was sensitive at as few as 20 copies of gDNA, a level more sensitive than the desired sensitivity of a clinical smear positive specimen which usually contains at least 1000 bacteria.

TABLE 1

| gDNA Copies per Reaction | Detected RLU |
| --- | --- |
| 0 (negative control) | $4.17 \times 10^3$ |
| 20 | $3.57 \times 10^4$ |
| 200 | $3.96 \times 10^5$ |
| 1000 | $1.31 \times 10^6$ |

In other experiments, the rpoB region was amplified similarly but using a combination of amplification oligonucleotides of SEQ ID NO:1 as a helper oligomer, SEQ ID NO: 2 as a promoter primer, and SEQ ID NO:8 (CG-GCACGCTCACGTG) as primer. The sensitivity of the assay in these experiments, as detected by hybridization with an AE-labeled probe, was at least about 200 copies of target per reaction. In these experiments, the target was provided at 800, 500 and 200 copies per reaction (5 reactions for each condition). All reactions gave positive results ($7.88 \times 10^3$ to $2.66 \times 10^6$ mean RLU) compared to the negative controls with no *M. tuberculosis* DNA in the reaction (which produced $1.93 \times 10^3$ mean RLU for two reactions).

EXAMPLE 2

Specificity of Amplification

This example shows the specificity of the amplification oligomers as demonstrated using a TMA reaction performed using amplification oligomers and procedures substantially as described in Example 1 and above. The target sequence for this assay was purified *Mycobacterium* gDNA extracted from bacteria obtained from the American Type Culture Collection ("ATCC", Manassas, Va.) or the Deutsche Sammlung von Mikroorganismen und Zellkulturen GmbH culture collection ("DSM", Braunschweig, Germany) and grown in vitro using standard microbiology procedures. The species tested included: *M. tuberculosis* (ATCC No. 27294), *M. kansasii* (DSM No. 43224), *M. avium* (ATCC No. 25291), and *M. gordonae* (ATCC No. 14470). In the amplification reactions, the target DNA were provided at 200, $10^3$, $10^4$, $10^5$, and $10^6$ copies per assay. The negative control reaction contained no *Mycobacterium* DNA and an equal volume of water was substituted for the sample volume.

For detection of the amplified nucleic acid, the homogeneous detection assay using a labeled probe as described in Example 1 was used except that undiluted labeled probe was used. The average RLU results (four assays per species DNA) obtained from these assays are shown in Table 2. For these, a signal of $5 \times 10^4$ RLU or greater was considered positive.

TABLE 2

| Copies of Target per reaction | Signal Detection Results (RLU) Obtained with *Mycobacterium* species | | | |
|---|---|---|---|---|
| | *M. tuberculosis* | *M. kansasii* | *M. avium* | *M. gordonae* |
| 0 | | $4 \times 10^3$ | | |
| 200 | $4.78 \times 10^6$ | Not Tested | Not Tested | Not Tested |
| $10^3$ | Not Tested | $1.37 \times 10^4$ | $1.37 \times 10^4$ | $1.34 \times 10^4$ |
| $10^4$ | Not Tested | $1.68 \times 10^4$ | $1.67 \times 10^4$ | $1.51 \times 10^4$ |
| $10^5$ | Not Tested | $1.40 \times 10^4$ | $1.41 \times 10^4$ | $1.27 \times 10^4$ |

As shown by the results in Table 2, the assay amplified and detected 200 copies of *M. tuberculosis* DNA in the reactions. For all of the other *Mycobacterium* species assayed, the results were negative even when much more target DNA was used ($10^3$ to $10^5$ copies per reaction). Thus, the specificity for *M. tuberculosis* using these amplification oligomers and probe was demonstrated by the minimal detectable signal obtained for the other *Mycobacterium* species even when more DNA was provided.

Using the same amplification procedures as described immediately above, the amplicons were also detected on a DNA probe array. Amplicons are chemically fragmented and fluorescently labeled using procedures substantially as previously described (PCT No. WO 01/44507 (Laayoun et al.)). The labeled fragments were detected on the DNA probe array using the GENECHIP□ System for detecting *M. tuberculosis* sequences as described above.

For each species tested, the results shown in Table 3 present the percentage of correct base calling that is used to identify a predetermined sequence diagnostic of *M. tuberculosis*. For amplicons obtained from sample DNA from each of the *Mycobacterium* species listed in Table 3, the relative amount of correct base calling on the *M. tuberculosis*-specific DNA probe chip is shown, with the average signal intensity for the detected signal (mean relative fluorescence units or RFU). A result of greater than 85% base calling is considered positive identification of the *M. tuberculosis* sequence.

The results obtained with this probe array detection system confirmed that the labeled probe detection results obtained with the homogeneous detection assay discussed above, and further confirmed that the amplification was specific for *M. tuberculosis*.

TABLE 3

| Species | *M. tuberculosis*-specific Base Calling % | Intensity (RFU) |
|---|---|---|
| *M. tuberculosis* | 96.7 | 3146 |
| *M. kansasii* | 9.8 | 92 |
| *M. avium* | 11.4 | 60 |
| *M. gordonae* | 13 | 125 |

EXAMPLE 3

Detection of Mutant Clones

This example shows the detection of rpoB sequences after target capture, amplification and detection. Detection was done by using labeled probe binding in a homogeneous detection assay and by binding labeled amplicons to a DNA probe array, substantially as described in Example 2. For detection, the same amplification reaction for each clone was divided into two parts.

The bacterial rpoB clones to be detected were generated from cloned rpoB sequences contained in a fragment of about 700 bp which was amplifed by the PCR and ligated into a plasmid vector (pGEM□-T EASY, Promega, Madison, Wis.) as described by Troesch et al. (*J. Clin. Microbiol.*, 1999, 37: 49-55). The insert DNA was sequenced. Clones containing known mutations served as the *M. tuberculosis* target sequence for target capture, amplification and detection using the procedures described above.

In the results shown in Table 4, a mutation detected in a cloned rpoB sequence is identified by the amino acid substitution (one letter code) and the position of the codon as described by Troesch et al. (id.). For example, "Q513L" means that a mutation affected position 513 relative to the initiation codon, which has a glutamine (Q) in a wild type strain but has a leucine (L) substitution in this mutant. Column 1 shows the expected sequence based on the independent sequencing of the cloned insert, and column 2 shows the results determined by hybridization of amplicons to the DNA probe array. The percentage of base calling (BC %) and the signal intensity (RFU) observed on the probe array for each clone are shown in columns 3 and 4, respectively. Column 5 shows the relative amount of *M. tuberculosis* amplicons obtained for each clone in one assay, as determined by hybridization to an AE-labeled probe and detected as relative light units (RLU) as described above. The results in Table 4 show that the amplification and detection methods result in correct identification of different variations that occur in rpoB sequences of *M. tuberculosis* mutants.

TABLE 4

| | DNA probe array results | | | HPA results |
|---|---|---|---|---|
| Expected | Observed | BC % | Intensity (RFU) | RLU |
| F505L/L511P/ S531C | F505L/L511P/ S531C | 100 | 2,535 | $7.51 \times 10^6$ |
| Q513L | Q513L | 86.2 | 1,315 | $3.50 \times 10^6$ |
| H526D | H526D | 94.3 | 2,285 | $9.63 \times 10^6$ |
| D516Y | D516Y | 95.1 | 1,182 | $7.94 \times 10^6$ |
| H526Y | H526Y | 97.6 | 3,108 | $5.66 \times 10^6$ |
| L511P | L511P | 92.7 | 1,774 | $4.74 \times 10^6$ |
| H526R | H526R | 96.7 | 3,422 | $7.44 \times 10^6$ |

EXAMPLE 4

Detection of *M. tuberculosis* in Clinical Specimen

This example shows the sensitivity of primers of the present invention when used in TMA amplification of clinical samples containing wild type *M. tuberculosis* and detection of the amplified RNA. Amplification was done substantially as described in Example 1. Amplicons were detected substantially as described in Example 2 on a solid support having an array of immobilized probes (GENECHIP™) and in a homogeneous detection assay with a labeled probe.

Positive sediments of *M. tuberculosis* (wild type) were obtained from sputum clinical specimens after digestion and decontamination of the sample. Most specimens received for mycobacterial culture contain various amounts of organic debris and a variety of contaminating, normal, or transient bacterial flora. A chemical decontamination process kills the contaminants while allowing recovery of the mycobacteria. The digestion and decontamination method was the standard N-Acetyl-L-Cysteine-2% sodium hydroxide (NALC-NaOH) procedure (Kent et al., 1985. *Public health mycobacteriology. a guide for level III laboratory*. US Dept of Health and Human Services, Centers for Disease Control, Atlanta, Ga.). NALC acts as a mucolytic agent to ensure liquefaction of the specimen and sodium hydroxide is a decontaminating agent. Smear intensity was determined based on the usual clinical classification of mycobacteria culture where "1+" means a low positive and "4+" means a high positive.

The results obtained for 12 specimens are summarized in Table 5. The results show the smear intensity for each specimen (column 2) compared to the probe detection results obtained with the homogeneous detection assay with a labeled probe (single assay RLU results, column 3) and the results obtained following hybridization to the DNA probe array (column 4, BC %, and column 5, signal intensity).

TABLE 5

| | | Labeled Probe | DNA Probe Array Result | |
|---|---|---|---|---|
| Specimen No. | Smear Intensity | Result RLU | BC % | Signal Intensity |
| Sediment 1 | 3+ | $6.37 \times 10^6$ | 97.6 | 30,734 |
| Sediment 2 | 3+ | $5.60 \times 10^6$ | 95.9 | 27,284 |
| Sediment 3 | 3+ | $1.09 \times 10^5$ | 94.3 | 1,046 |
| Sediment 4 | 4+ | $2.36 \times 10^6$ | 99.2 | 12,702 |
| Sediment 5 | 4+ | $6.86 \times 10^5$ | 98.4 | 8,273 |
| Sediment 6 | 4+ | $3.90 \times 10^6$ | 98.4 | 17,204 |
| Sediment 7 | 4+ | $6.02 \times 10^6$ | 99.2 | 8,619 |
| Sediment 8 | 3+ | $4.867 \times 10^6$ | 99.2 | 6,391 |
| Sediment 9 | 3+ | $2.99 \times 10^6$ | 98.4 | 5,178 |
| Sediment 10 | 3+ | $1.98 \times 10^6$ | 99.2 | 3,196 |
| Sediment 11 | 2+ | $2.08 \times 10^6$ | 96.7 | 820 |
| Sediment 12 | 2+ | $3.50 \times 10^6$ | 98.4 | 2,615 |

The results shown in Table 5 demonstrate the efficiency of amplification with clinical specimens. For all sediments tested, the labeled probe detection results (RLU) were all positive compared to a negative control (not shown), and the DNA probe array detection results were similarly positive. In the probe array analysis, all of the tested sediments were detected as wild type *M. tuberculosis.*

EXAMPLE 5

PCR Amplification and Detection of Amplicons

This example shows the sensitivity of primers of the present invention when used in another amplification method, the polymerase chain reaction (PCR). The amplified DNA was detected on a solid support having an array of immobilized probes (i.e., GENECHIP™). For target preparation, wild type *M. tuberculosis* (ATCC No. 27177) was grown in vitro using standard microbiology methods. Bacterial stock suspensions were made in water and adjusted to a concentration of about $6\times10^8$ bacteria per ml. Successive dilutions in water were made to produce a concentration of $10^4$ bacteria per µl (equivalent to $10^4$ copies of bacterial DNA per µl) which were then inactivated by heating for 15 min at 95° C.

PCR amplification was carried out in a plastic tube using a thermostable DNA polymerase isolated from *Thermus aquaticus* (FAST START□ Taq DNA polymerase, Roche Molecular Biochemicals). Briefly, the amplification mixture (50 µl final volume) contained 5 µl of 10× amp buffer, 0.4 µl of dNTP mix (25 mM each of ATP, CTP, UTP and GTP), 1.5 µl each of primers of SEQ ID NO:2 and SEQ ID NO:3 (10 µM), 0.4 µl of DNA polymerase (2U), 5 µl of target (or water for the negative control). Thermal cycling was performed using an automated thermal cycler (PERKIN-ELMER 9600™) with an initial denaturation step at 95° C. for 4 min, followed by 35 cycles each consisting of 95° C. for 30 sec, 50° C. for 30 sec and 72° C. for 45 se cycle of 72° C. for 7 min.

Following PCR amplification, the amplification products were analyzed by agarose gel electrophoresis and stained with ethidium bromide, to detect the presence or absence of a 168 nt band of amplified DNA. No band was visible on the gel for the negative control (i.e., without target DNA). A DNA band was seen when a reaction included $10^4$ or more copies of target.

Next, amplification products were detected on a DNA probe array (GENECHIP™), substantially as described previously (Troesch et al., 1999, *J. Clin. Microbiol.* 37(1):49-55). Promoter-tagged PCR amplicons were used to generate single-stranded RNA targets by in vitro transcription reactions (20 µl) that each contained about 50 ng of PCR product, 20 U of T7 RNA polymerase (Promega), 40 mM Tris acetate (pH 8.1), 100 mM $Mg(acetate)_2$, 10 mM dithiothreitol, 1.25 mM each of ATP, CTP, UTP and GTP, and were incubated at 37° C. for 1 hr.

The RNA was fluorescently labeled substantially as described (PCT No. WO 01/44507) and the labeled RNA was hybridized to the probe array and analyzed (Troesch et al., supra). For hybridization, 5 µl the labeled RNA was diluted in 700 µl of hybridization buffer (0.90 M NaCl, 60 mM $NaH_2PO_4$, 6 mM EDTA, pH 7.4, and 0.05% (v/v) TRITON® X-100), applied to the probe array and incubated at 45° C. for 30 min. Then the probe array was washed twice in 3×SSPE (0.45 M NaCl, 30 mM $NaH_2PO_4$, 3 mM EDTA, pH 7.4) and 0.005% (v/v) TRITON® X-100 at 30° C. and the fluorescent signal bound to the array was detected. The detected signal intensities (mean, median and maximum RFU), nucleotide % base calling and sequence determinations were generated by using the system algorithm (GENECHIP™ software, Affymetrix). A candidate selection index was determined by the percentage of homology between the experimentally derived sequence and reference sequences present on the array. The results obtained from this experiment showed that for $10^4$ copies of target the sequence determined on the probe array was that of wild type *M. tuberculosis*, based on 91.9% base calling and a signal intensity of 1312 RFU, compared to the background signal of 101 RFU.

EXAMPLE 6

Amplification of rpoB (+) Strand Target

This example shows that the assay can amplify and detect amplicons made from the rpoB region but from the (+) DNA strand for comparison to the (−) DNA strand amplification described in Example 1. Using substantially the same amplification conditions as in Example 1, the amplification oligonucleotides used in the (+) strand amplification reaction were: SEQ ID NO:10 (AATTTAATACGACTCACTATAGGGAGAACGCTCACGTGACAGAC) as a promoter primer and SEQ ID NO: 11 (GGTCGCCGCGATCAAG) as a primer. The target sequences for this assay were purified gDNA extracted from a lysed bacterial culture of *M. tuberculosis* and provided at $5\times10^3$ copies per amplification reaction or a crude lysate of sonicated *M. tuberculosis* cells grown in broth culture, provided at about $5\times10^3$ copies per amplification reaction. As a negative control, an equal volume of water containing no *M. tuberculosis* DNA was substituted for the DNA-containing samples in a separate amplification reaction that was processed as for the positive samples. Amplification was assessed based on the detected chemiluminescence (RLU) after a homogeneous detection assay performed substantially as described above but using the AE-labeled detection probe of SEQ ID NO:12 (CATGAATTGGCTCAGCTG). For both the purified gDNA and the crude lysate samples, positive signals were detected. For two replicate assays with purified gDNA targets the average signal detected was $5.66\times10^6$ RLU, and for five replicate assays with crude lysate DNA targets the average signal detected was $5.25\times10^6$ RLU. The negative control (two replicate assays) gave $6.15\times10^2$ RLU. These results show that the assay can specifically detect rpoB sequences independent of the strand of *M. tuberculosis* DNA that is amplified.

We claim:

1. A method of detecting rpoB sequences of *Mycobacterium tuberculosis* present in a biological sample, comprising the steps of: providing a biological sample containing nucleic acid from *M. tuberculosis* comprising a rpoB sequence; amplifying the rpoB sequence in an in vitro nucleic acid amplification reaction mixture comprising at least one polymerase activity, and a first primer consisting of SEQ ID NO: 2 and a second primer consisting of SEQ ID NO: 8 to produce amplified nucleic acid containing a rpoB sequence; optionally fragmenting the amplified nucleic acid; hybridizing the amplified nucleic acid to at least one detection probe consisting of SEQ ID NO:4 that hybridizes specifically to *M. tuberculosis* sequences; and detecting the amplified nucleic acid hybridized to at least one detection probe by detecting a label associated with the amplified nucleic acid, thereby detecting the rpoB sequences of *Mycobacterium tuberculosis* present in the biological sample.

2. The method of claim 1, before the amplifying step, further comprising the steps of: adding to the biological sample a combination of first and second capture oligomers consisting of SEQ ID NO: 5 and SEQ ID NO: 6 wherein the first and second capture oligomers specifically hybridize to a *M. tuberculosis* sequence specific for each capture oligomer, and an immobilized nucleic acid that hybridizes to a 3' tail sequence of the first and second capture oligomers; hybridizing the nucleic acid from *M. tuberculosis*, the capture oligomers, and the immobilized nucleic acids to produce a hybridization complex comprising the nucleic acid from *M. tuberculosis,* at least one of the first and second capture oligomers, and the immobilized nucleic acid; and separating the hybridization complex from other components of the biological sample.

3. The method of claim 1, wherein the amplifying step uses a helper oligomer consisting of SEQ ID NO: 1.

4. The method of claim 1, wherein amplifying comprises transcription-mediated amplification.

5. The method of claim 1, wherein amplifying comprises polymerase chain reaction (PCR) amplification.

6. The method of claim 1, wherein the method includes chemically fragmenting the amplified nucleic acid and fluorescently labeling fragments of the amplified nucleic acid.

7. A composition for detecting a rpoB sequence of *M. tuberculosis*, comprising an oligonucleotide consisting of SEQ ID NO: 2, an oligonucleotide consisting of SEQ ID NO 8, and optionally at least one detection probe consisting of SEQ ID NO: 4.

8. The composition of claim 7, further comprising an oligonucleotide consisting of SEQ ID NO: 1.

9. The composition of claim 7, further comprising a combination of a first oligonucleotide consisting of SEQ ID NO: 5 and a second oligonucleotide consisting of SEQ ID NO: 6.

10. A kit comprising: an oligonucleotide consisting of SEQ ID NO: 2, an oligonucleotide consisting of SEQ ID NO: 8, and at least one oligonucleotide selected from the group consisting of an oligonucleotide consisting of SEQ ID NO: 1 and an oligonucleotide consisting of SEQ ID NO: 4.

11. The kit of claim 10, comprising the oligonucleotide consisting of SEQ ID NO: 1.

12. The kit of claim 10, comprising the oligonucleotide consisting of SEQ ID NO: 4.

13. The kit of claim 10, further comprising an oligonucleotide consisting of SEQ ID NO: 5 and an oligonucleotide consisting of SEQ ID NO: 6.

14. The kit of claim 10, further comprising an oligonucleotide consisting of SEQ ID NO: 10 or an oligonucleotide consisting of SEQ ID NO: 11.

15. The kit of claim 10, comprising an oligonucleotide consisting of SEQ ID NO: 1 and an oligonucleotide consisting of SEQ ID NO: 4.

* * * * *

SEQUENCE LISTING

```
<160> NUMBER OF SEQ ID NOS: 12

<210> SEQ ID NO 1
<211> LENGTH: 16
<212> TYPE: DNA
<213> ORGANISM: Artificial Sequence
<220> FEATURE:
<223> OTHER INFORMATION: primer oligonucleotide

<400> SEQUENCE: 1
gaccacccag gacgtg                                                      16

<210> SEQ ID NO 2
<211> LENGTH: 47
<212> TYPE: DNA
<213> ORGANISM: Artificial Sequence
<220> FEATURE:
<223> OTHER INFORMATION: primer oligonucleotide
<220> FEATURE:
<221> NAME/KEY: promoter
<222> LOCATION: (1)..(27)

<400> SEQUENCE: 2
aatttaatac gactcactat agggagacga tcacaccgca gacgttg                    47

<210> SEQ ID NO 3
<211> LENGTH: 15
<212> TYPE: DNA
<213> ORGANISM: Artificial Sequence
<220> FEATURE:
<223> OTHER INFORMATION: primer oligonucleotide

<400> SEQUENCE: 3
gctcgcgctc acgtg                                                       15

<210> SEQ ID NO 4
<211> LENGTH: 18
<212> TYPE: DNA
<213> ORGANISM: Artificial Sequence
<220> FEATURE:
<223> OTHER INFORMATION: detection probe oligonucleotide
<220> FEATURE:
<221> NAME/KEY: misc_feature
<222> LOCATION: (1)..(18)
<223> OTHER INFORMATION: 2'-methoxy linkages in oligonucleotide backbone

<400> SEQUENCE: 4
gttgttctgg tccatgaa                                                    18
```

```
<210> SEQ ID NO 5
<211> LENGTH: 64
<212> TYPE: DNA
<213> ORGANISM: Artificial Sequence
<220> FEATURE:
<223> OTHER INFORMATION: capture oligonucleotide

<400> SEQUENCE: 5
ggccaccatc gaatatctgg tccgcttgca ctttaaaaaa aaaaaaaaaa aaaaaaaaaa      60
aaaa                                                                  64

<210> SEQ ID NO 6
<211> LENGTH: 55
<212> TYPE: DNA
<213> ORGANISM: Artificial Sequence
<220> FEATURE:
<223> OTHER INFORMATION: capture oligonucleotide

<400> SEQUENCE: 6
catgtcgcgg atggagcggg tggtcaaaaa aaaaaaaaaa aaaaaaaaa aaaaa           55

<210> SEQ ID NO 7
<211> LENGTH: 27
<212> TYPE: DNA
<213> ORGANISM: Artificial Sequence
<220> FEATURE:
<223> OTHER INFORMATION: synthetic oligonucleotide
<220> FEATURE:
<221> NAME/KEY: promoter
<222> LOCATION: (1)..(27)
<223> OTHER INFORMATION: T7 RNA polymerase promoter

<400> SEQUENCE: 7
aatttaatac gactcactat agggaga                                         27

<210> SEQ ID NO 8
<211> LENGTH: 15
<212> TYPE: DNA
<213> ORGANISM: Artificial Sequence
<220> FEATURE:
<223> OTHER INFORMATION: primer oligonucleotide

<400> SEQUENCE: 8
cggcacgctc acgtg                                                      15

<210> SEQ ID NO 9
<211> LENGTH: 55
<212> TYPE: DNA
<213> ORGANISM: Artificial Sequence
<220> FEATURE:
<223> OTHER INFORMATION: capture oligonucleotide

<400> SEQUENCE: 9
catcgaatat ctggtccgct tgcacaaaaa aaaaaaaaaa aaaaaaaaa aaaaa            55

<210> SEQ ID NO 10
<211> LENGTH: 44
<212> TYPE: DNA
<213> ORGANISM: Artificial Sequence
<220> FEATURE:
<223> OTHER INFORMATION: primer oligonucleotide
<220> FEATURE:
<221> NAME/KEY: promoter
<222> LOCATION: (1)..(27)
<223> OTHER INFORMATION: T7 RNA polymerase promoter

<400> SEQUENCE: 10
```

-continued

```
aatttaatac gactcactat agggagaacg ctcacgtgac agac                44

<210> SEQ ID NO 11
<211> LENGTH: 16
<212> TYPE: DNA
<213> ORGANISM: Artificial Sequence
<220> FEATURE:
<223> OTHER INFORMATION: primer oligonucleotide

<400> SEQUENCE: 11
ggtcgccgcg atcaag                                                16

<210> SEQ ID NO 12
<211> LENGTH: 18
<212> TYPE: DNA
<213> ORGANISM: Artificial Sequence
<220> FEATURE:
<223> OTHER INFORMATION: detection probe oligonucleotide

<400> SEQUENCE: 12
catgaattgg ctcagctg                                              18
```